United States Patent
Rødtness et al.

(10) Patent No.: US 10,173,219 B2
(45) Date of Patent: Jan. 8, 2019

(54) BREAKABLE VESSEL FOR SAMPLE STORAGE

(75) Inventors: Allan Rødtness, Odense M (DK);
Anders Rørdam Michelsen, Viby Sj. (DK); Henrik Neuschäfer Larsen, Søborg (DK)

(73) Assignee: 1CryoBio AG, Platz (CH)

( * ) Notice: Subject to any disclaimer, the term of this patent is extended or adjusted under 35 U.S.C. 154(b) by 891 days.

(21) Appl. No.: 13/983,834

(22) PCT Filed: Feb. 3, 2012

(86) PCT No.: PCT/DK2012/050043
§ 371 (c)(1),
(2), (4) Date: Aug. 6, 2013

(87) PCT Pub. No.: WO2012/107046
PCT Pub. Date: Aug. 16, 2012

(65) Prior Publication Data
US 2013/0312372 A1    Nov. 28, 2013

(30) Foreign Application Priority Data

Feb. 7, 2011 (DK) .................................. 2011 70069

(51) Int. Cl.
*B01L 3/00* (2006.01)
*G01N 1/42* (2006.01)

(52) U.S. Cl.
CPC ......... *B01L 3/50855* (2013.01); *B01L 3/5085* (2013.01); *G01N 1/42* (2013.01);
(Continued)

(58) Field of Classification Search
CPC .. B01L 3/502; B01L 3/50825; B01L 3/50855; B01L 2300/0861; B01L 2300/087
(Continued)

(56) References Cited

U.S. PATENT DOCUMENTS 3,750,645 A    8/1973    Bennett et al.
4,883,452 A    11/1989   Kasai et al.
(Continued)

FOREIGN PATENT DOCUMENTS

| GB | 2015158 A | 9/1979 |
| WO | WO-2009/086829 A2 | 7/2009 |
| WO | WO-2010/131880 A2 | 11/2010 |

OTHER PUBLICATIONS

International Search Report and Written Opinion for International Patent Application No. PCT/DK2012/050043, dated May 14, 2012 (12 pages).

*Primary Examiner* — Jill A Warden
*Assistant Examiner* — Dwayne K Handy
(74) *Attorney, Agent, or Firm* — Dinsmore & Shohl LLP

(57) ABSTRACT

The present invention relates to a vessel for containing and storing a sample and subsequent easy access to individual specimens of the sample, in particular specimens of biological samples. One embodiment discloses a breakable multi-specimen storage vessel comprising a container comprising a lower end and an upper end, at least one end having an open end, the length of said container being continuously formed and provided with break portions at predetermined positions alongside thereof where said container is adapted to be broken into a plurality of specimens, each specimen having a first end provided with at least a part of a first fastening mechanism and a second end provided with at least a part of a second fastening mechanism, wherein the configuration of the first fastening mechanism is different from the configuration of the second fastening mechanism. The breakable storage vessel according to the present invention may be applied within cryogenic storage applications.

33 Claims, 3 Drawing Sheets

(52) U.S. Cl.
CPC ..... *B01L 3/50825* (2013.01); *B01L 2200/087* (2013.01); *B01L 2300/042* (2013.01); *B01L 2300/0832* (2013.01); *B01L 2300/0861* (2013.01)

(58) Field of Classification Search
USPC ................................. 422/547, 549, 558, 559
See application file for complete search history.

(56) References Cited

U.S. PATENT DOCUMENTS

| | | | |
|---|---|---|---|
| 4,984,430 A | 1/1991 | Kuraoka et al. | |
| 4,987,921 A | 1/1991 | Kasai et al. | |
| 5,221,267 A | 6/1993 | Folden | |
| 6,383,453 B1 | 5/2002 | Banauch et al. | |
| 2002/0009390 A1* | 1/2002 | Lappe | B01L 3/502 436/165 |
| 2007/0269341 A1* | 11/2007 | Halverson | G01N 1/34 422/400 |
| 2010/0303688 A1 | 12/2010 | Andersen | |

\* cited by examiner

BREAKABLE VESSEL FOR SAMPLE STORAGE

CROSS-REFERENCE TO RELATED APPLICATION

This application is the U.S. national stage filing under 35 U.S.C. § 371 of International Application No. PCT/DK2012/050043, filed Feb. 3, 2012, which claims the benefit of the filing date of Danish Patent Application No. PA 2011 70069, filed Feb. 7, 2011.

The present invention relates to a vessel for containing and storing a sample and subsequent easy access to individual specimens of the sample, in particular specimens of biological samples. The breakable storage vessel according to the present invention may be applied within cryogenic storage applications.

BACKGROUND OF INVENTION

Biological samples, such as substances in solution, e.g. blood samples, water tests, and tissue samples such as fertilized embryos, can often be effectively stabilized by freezing. The frozen fluid and/or sample will remain stable for extended periods of time as long as it is kept in the frozen state. Frequently these samples are collected in relatively large quantities, or collective sample, but could be utilized in smaller quantities, or specimens e.g. for test purposes.

When a specimen is needed, it often requires thawing of the entire collective sample to obtain the specimen currently needed, and then refreezing the remainder of the collective sample. However, frequent freezing and thawing cycles are almost always detrimental to the often unstable ingredients in the collective sample.

One solution is to store the collective sample in multiple small individual vessels. Then, when a specimen is needed, the necessary number of individual vessels may be thawed to provide the specimen needed without thawing and refreezing other individual samples of the collective sample. However, separation and freezing in individual vessels is cumbersome and time consuming, requires a larger amount of individual vessels, and thus larger storage facilities. The chance of confusion and mix-up of the individual vessels is also present.

U.S. Pat. No. 6,383,453 discloses a multi-specimen storage vessel provided with a number of equally distanced ring-shaped "notches" that extend around the perimeter of the vessel to constitute breakpoints. External screw threads for closing each specimen with screw caps may be provided on the ends of each specimen, i.e. surrounding the breakpoints. WO 2009/086829 discloses a breakable multi-specimen storage vessel comprising a container provided with break portions at predetermined positions alongside whereby the container is adapted to be broken into to a plurality of specimens. The vessel and a broken off specimen may be closed by closure caps.

SUMMARY OF INVENTION

A problem with the breakable storage vessels known in the art is that when a specimen containing a biological sample is broken off and subsequently closed at each end with e.g. caps the biological sample is consequently accessible from both sides of the specimen. This may cause unfavourable situations, e.g. if the bottom end of a specimen is opened by mistake leading to potential loss of the sample. This may be avoided by the improved storage vessel of the present invention: A breakable multi-specimen storage vessel comprising a container comprising a lower end and an upper end, at least one end having an open end, the length of said container being continuously formed and provided with break portions at predetermined positions alongside thereof where said container is adapted to be broken into a plurality of specimens, each specimen having a first end provided with at least a part of a first fastening mechanism and a second end provided with at least a part of a second fastening mechanism, wherein the configuration of the first fastening mechanism is different from the configuration of the second fastening mechanism.

The present invention further relates to a method for closing and safely reopening a storage container comprising at least two open ends, wherein a first end is provided with at least a part of a first fastening mechanism and a second end is provided with at least a part of a second fastening mechanism, and wherein the configuration of the first fastening mechanism is adapted to be different from the configuration of the second fastening mechanism such that upon closing of the container only one of the first end and the second end can be easily reopened.

With different configurations of the fastening mechanism at each end of a specimen the access to the content of the specimen is different depending on which end of the specimen is dealt with. This enables a more secure handling of biological samples because it can be ascertained which end of the specimen will open.

DETAILED DESCRIPTION OF THE INVENTION

In the preferred embodiment of the invention the container has a circular cross section. However, other cross sections may be provided, such as an elliptical cross section polygonal cross section.

A fastening mechanism is a mechanism used to fasten two parts together. E.g. a screw thread is the fastening mechanism that enables that a screw bolt can join the matching nut.

In the preferred embodiment of the invention the storage vessel further comprises closure means adapted to close and/or seal the container and/or one or more of said specimens. Preferably said closure means comprise or constitute the corresponding part of the second fastening mechanism. By the "corresponding part" in the meaning of the attachment part, the receptor part, the fastener part, and/or the mating part of the first and/or the second fastening mechanism. Thus, preferably the closure means is adapted to engage with the container and the ends of each specimen by means of the first and/or the second fastening mechanisms. The closure means may for example be one or more caps. Preferably said closure means provides a liquid and air-tight seal between closure means and container/specimen.

It might be necessary to provide additional sealing to ensure a liquid and/or air-tight seal between the closure means and a specimen. Thus, in a further embodiment of the invention the closure means and/or the ends of a breakpoint are further provided with sealing means adapted to seal the connection between the closure means and the container and/or one or more of said specimens. Thus, the fastening mechanism provides the fastening and the sealing means provides the seal. In the preferred embodiment of the invention engagement of the fastening mechanism provides "activation" of the sealing means, i.e. closing of the fastening mechanism results in a liquid and/or air-tight seal between the closure means and a specimen due to the sealing means.

In one embodiment of the invention the sealing means is at least a part of a snap type connection, said snap type connection preferably comprising a "plug" (male part) fitting into a "socket" (female part). Thus, each end of a specimen may comprise or constitute a male part of said snap connection and where the corresponding female part of said snap connection is provided integral with the closure means. Thus, when the closure means is engaged with a specimen by means of the fastening mechanism the snap type connection is engaged provided the sealing. In order to provide an even better sealing the sealing means may comprise a material that is softer than the material of (the rest of) the closure means. I.e. said sealing means may be at least partly provided in a material that is softer than the material of (the rest of) the closure means. E.g. the female part of the snap type connection may be at least provided in a material that is softer than the material of (the rest of) the closure means. The softer female part then provides an additional sealing effect, like a lid provided with a rubber packing or gasket.

The storage vessel according to the invention, including the closure means, may be manufactured by means of injection moulding. A closure means comprising materials of different hardness, e.g. for the sealing means, may correspondingly be manufactured by means of multi component injection moulding.

In one embodiment of the invention said part of the first and/or second fastening mechanism is provided on the outer surface of the first and/or second end of a specimen. Further, the configuration of the part of the first fastening mechanism provided on the first end of a specimen may be different from the configuration of the part of the second fastening mechanism provided on the second end of a specimen. The term "configuration" here in the meaning of any of the terms: layout, shape, outer shape, external form, exterior, design, construction and elaboration. Thus, the layout, shape, outer shape, external form, exterior, design, construction and/or elaboration of the part of the first fastening mechanism provided on the first end of a specimen may be different from the layout, shape, outer shape, external form, exterior, design, construction and/or elaboration of the part of the second fastening mechanism provided on the second end of a specimen. Thus, the difference in configuration of the first and second fastening mechanisms may be due to different fastening mechanism parts provided on the specimens. Further, the part of the first fastening mechanism provided on the first end of a specimen and the part of the second fastening mechanism provided on the second end of a specimen may be adapted to match the same receptor/attachment/fastener. Thus, even though the fastening mechanism parts provided on the specimens is configured differently they still fit the same receptor. I.e. the same closure means may be used for both ends of a specimen.

In one embodiment of the invention the first or the second fastening mechanism is a locking mechanism. In this case a locking mechanism is understood as a fastening mechanism that locks, i.e. once the fastening mechanism is closed it is very difficult to reopen. Thereby it may be ensured that after closing a broken off specimen only one end of the specimen is accessible, because only one end can be reopened/unlocked.

In a further embodiment of the embodiment of the invention the tension of the first fastening mechanism is different from the tension of the second fastening mechanism.

Tension of a fastening mechanism is understood as the tensional power needed to close and/or release the fastening mechanism. Thus, with different tension of the first and second fastening mechanisms it may be ensured that one specific end of closed specimen is accessed.

In one embodiment of the invention the first and/or the second fastening mechanism is a bayonet mount. A bayonet mount (or bayonet connector) is a fastening mechanism consisting of a male side with one or more pins, and a female receptor with matching L slots. The mount may be provided with resilient means (such as a spring) to better keep the two parts together. One of the advantages of a bayonet mount compared to e.g. a screw threaded mount is that typically only half a revolution between the two part is necessary to fasten the two parts together.

Preferably said part of said first and second fastening mechanism provided on the first and second end of each specimen, respectively, is the male side of a bayonet mount, i.e. one or more pins is provided at each end of a specimen, preferably provided on the outer surface of the specimen.

In one embodiment of the invention at least one pin of the bayonet mount is provided with a first protrusion. Preferably the pin(s) of the bayonet mount on one side of the specimen is provided with a first protrusion. The different pins provides for different configurations of the fastening mechanisms (bayonet mount) of the first and second side of a specimen. Preferably the closure means comprise the female side of the corresponding bayonet mount where the female part of the mount is provided with a groove adapted to match the corresponding male pin and a second protrusion in said groove adapted to engage with said first protrusion in the male part. Thus, both sides of the specimen are preferably provided with the male part of a bayonet mount and both sides of the specimen preferably match the closure means. However, the first protrusion at the pin(s) at one side of the specimen is adapted to engage with the second protrusion in the groove in the female part of the bayonet mount provided in the closure means. And when a bayonet mount comprising a pin with a first protrusion and a female mount with matching second protrusion groove is engaged the two protrusions engage to provide a locking effect. Thus, consequently one end of the specimen is substantially locked whereas the other end can be easily reopened.

A further advantage of a bayonet mount is that when the male part of the bayonet mount (i.e. the pins) is provided on the container the mount can be isolated from the break portion area. I.e. if the break is provided along the recesses there is a risk of minor rugged and fractured parts along the break area. However, as the bayonet pins can be provided on the outer surface of the container with a small distance to the recesses the pins may be unaffected by a break.

In one embodiment of the invention the closure means is one or more caps, preferably adapted to engage with the container and/or one or more of said specimens. Further, at least one of said caps may be a snap cap. A snap fastener may be a circular lip under one disc that fits into a groove on the top of the other, holding them fast until a certain amount of force is applied. Snap fasteners are often used in children's clothing, as they are relatively easy for children to use. The "snap" closing may be combined with the fastening mechanism to provide a better sealing.

In a further embodiment of the invention at least one of said caps is provided with an internal curving bottom. Further, the material of the cap may be softer than the material of the container or the material of the cap is harder than the material of the container.

In a preferred embodiment, the container is adapted to be broken into to a plurality of specimens by application of a radially directed force, however other breaking means may also be used, such as breaking by twisting, bending or combinations of the mentioned breaking means. The container includes the possibility of one or more, e.g. multiple break portions at which the container can be divided along with its contents into one or more specimens, comprising one or more break portions. The remaining samples can be stored or transported for processing or testing without having to be thawed and refrozen. In an embodiment of the storage vessel, said break portions are provided as a one or more ring-shaped external recesses extending around the perimeter of said tubular container. Thus, the break portions are easy to produce, e.g. by moulding, milling, etching or cutting, easy to break cleanly into specimens, and easy to place in relation to a break operation. The depth of said recesses may be ranging from 50% to 95%, preferably from 70% to 95%, more preferably from 80% to 90% of the total wall thickness of said container.

The internal surface of said container is preferably smooth, where smooth is defined as the inner surface of the container being provided without recesses and/or projecting parts outside production tolerances. By the provision of a substantially smooth inner surface, both in a longitudinal direction and going round the inside the container in general does not require any further processing other than being moulded and/or blown. Thus, the production process is eased and the production costs are reduced. By reducing the production costs of each individual vessel it may indeed also enable cost effective mass production thereof. The container is made of any suitable method, such as moulding or extrusion. Further, the container is easy to empty, clean, and dry during use. In general, the container is provided as a disposable device, but one or more parts thereof may be suitable for reuse, depending on application. It has by the invention been realized, that any size, length and diameter, and section shape, such as circular, triangular, square, hexagon or other polygon, may be broken off when provided as a container vessel according to the invention.

In a further embodiment of the invention the storage vessel comprises identification marks, such as arrows, for indicating the different configurations of the fastening mechanisms. Further, identification marks, such as arrows, may be provided on each specimen for indicating the different configuration of the fastening mechanisms.

In an embodiment of the storage vessel, two or more of said external recesses are provided equally distanced with a distance D, which distance range from between 1 to 100%, preferably from between 10 to 50%, more preferably from 33 to 40% of the entire length of the container. Thus, different size specimens may be broken off. It may be an advantage to place the recesses farther apart for providing a large volume of sample. However, it may on the other hand be more suitable to provide the recesses close together, e.g. 1-5 mm in between, to provide a wider selection of volumes to be broken off from the collective sample. Alternatively, the individual recesses are positioned sequentially, but not with an equal distance apart, e.g. for special applications using an increasing distance, e.g. doubling the distance.

In an embodiment of the storage vessel the closure means provided with an internal curving bottom. This provide easy access e.g. for a syringe needle in the bottom thereof, as the inner curving surface thus provides the bottom of the specimen broken off.

In an embodiment of the storage vessel, the material of the closure means is softer than the material of the container. In another, the material of the closure means is harder than the material of the container. Harder or softer is defined as the hardness during breakage temperatures, such as cryogenic temperatures, wherein cryogenic temperatures is used in its conventional meaning, i.e. below −80° C., such as below −150° C. This enables an easier attachment and detachment of the closure means to/from the container. Alternatively, the two materials have the same hardness, and may also even be the same material.

In an embodiment of the storage vessel, the tubular container material is a plastic material. Said plastic material may be selected from the group consisting of polyethylene and polypropylene. In another embodiment, the material of the tubular container is a glass material. These materials resist and conform well to cryo temperatures, resist chemical agents well, provide easy production thereof, and are non-toxic to the samples. Further, these materials provide a vessel, which is easy to break during freezing temperatures. Said storage vessel may be a cryogenic storage vessel, but need not be, for example when the vessel is used for storing a fluid, which is fluid at room temperature, but solid a temperatures around 5° C., such as stock for sauces, or when the fluid is crystalline at −3° C., but fluid above, such as water.

In general the storage vessel may be used for any material which physical state can change from one state, e.g. a liquid state, into a solid state, depending on the ambient conditions, such as temperature and pressure. For instance, in one embodiment, the material is a gel having a phase transition from liquid to solid at a temperature greater than 0° C.

In an embodiment of the storage vessel, at least the surface of said container is provided with identification markings for identifying at least the specimen taken, and/or identification markings for identifying at least the vessel, the specimen is taken from. In another embodiment said identification markings also marks the volume within.

Thus, each individual specimen may be identified and traced to the mother collective sample/vessel. Further, each individual vessel may be identified, among several identical vessels. The volume is then precisely indicated and may be used for breaking off the desired length of specimen.

DESCRIPTION OF DRAWINGS

In the following the invention is described with reference to some embodiments shown in the accompanying schematic drawings, in which.

DETAILED DESCRIPTION OF THE DRAWINGS

The following is with reference to all FIGS. 1-7 showing an exemplary and realized embodiment of the invention. The figures show how the general idea of the invention, i.e. having (parts of) fastening mechanisms with different configurations at the ends of a storage container, may be implemented by means of a bayonet mount. However, the present invention could also be realized by other types of fastening mechanisms, such as traditional threaded screw mounts.

Figure 1:
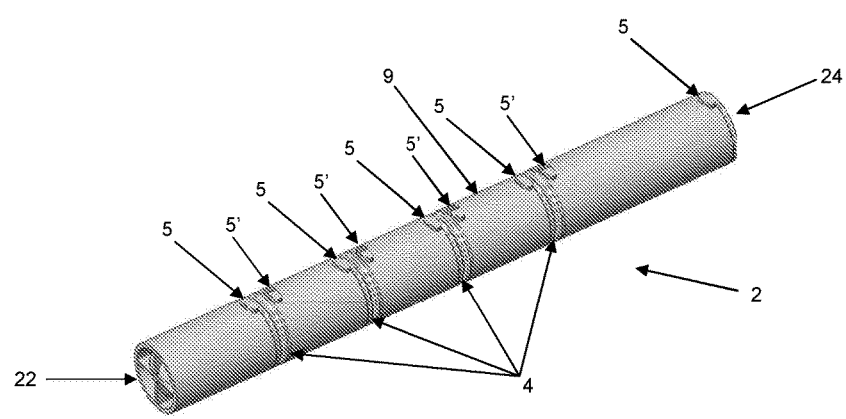
FIG. 1 is a perspective illustration of a breakable multi-specimen storage vessel according one embodiment of the invention.

FIG. 1 shows at least a part of a breakable multi-specimen storage vessel according to a first embodiment of the invention, suitable for containing a collective sample of e.g. a biological fluid sample and e.g. storing this at cryogenic temperatures. It is noted, that the vessel may be suitable for use in other applications, for example storing household or industrial cooking stock, as the vessel is used for storing a fluid, which is fluid at room temperature, but solid a temperatures around 5 degrees C., or for storing water bound samples, where the fluid is crystalline at −3 degrees C., but fluid above. Further, the samples kept within the vessel may be non-fluid and/or non-biological, as well, depending on application.

The storage vessel comprises a cylindrical longitudinally extending tubular container 2 having a container bottom 22 at a closed lower proximal end thereof and an open end 24. The container 2 in FIG. 1 is provided with four externally provided ring-shaped break portions 4 on a perimeter thereof which provides the possibility of breaking off five specimens in total from the vessel comprising the collective sample. The break portions 4 are formed as ring-shaped cuts or recesses extending approximately partly through the thickness of the wall material of the cylindrical tubular container 2. The plurality of break portions 4 is formed along the length of the container 2 between the bottom end 22 and the open top end 24. The break portions 4 separate the multi-specimen container 2 into individual specimens, which by breaking can be separated from the remainder of the collective sample as needed. The container wall interior opposite the break portions 4 have a longitudinally plane, smooth surface in order to provide as large an interior volume as possible and for facilitating a low-cost production thereof. By the term smooth is meant that the surface is provided substantially without recesses and/or projecting parts outside production tolerances, such as less than a few hundredth to less than a few thousandth of the wall thickness. The break portions 4 are designed to facilitate breakage of the container 2 at the break portions 4, since they constitute reduced wall thickness areas of the container 2.

Figure 2:
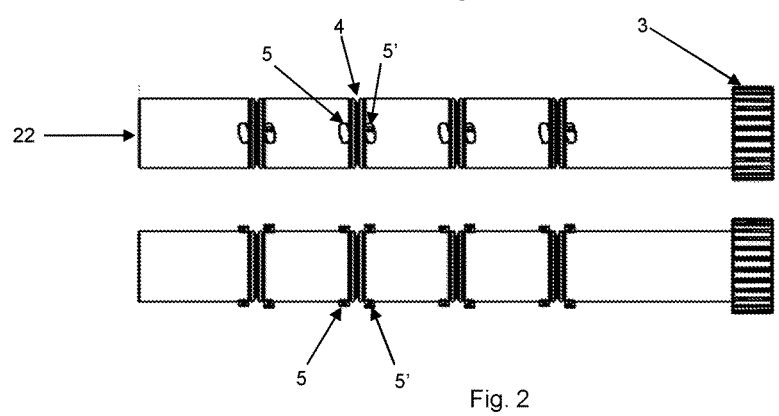
FIG. 2 shows top-view and side view schematic drawings of the breakable multi-specimen storage vessel of FIG. 1.
Figure 3:
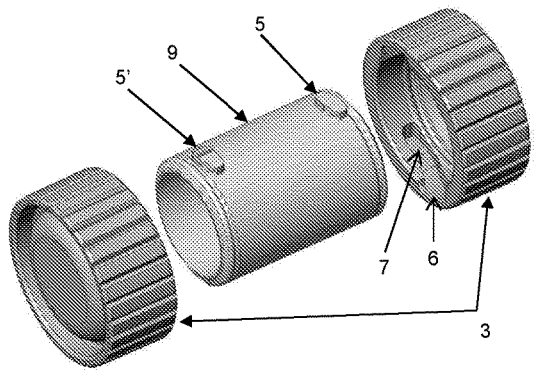
FIG. 3 is a perspective illustration of a broken off specimen of the storage vessel of FIG. 1 illustrated with matching closure caps.
Figure 5A:
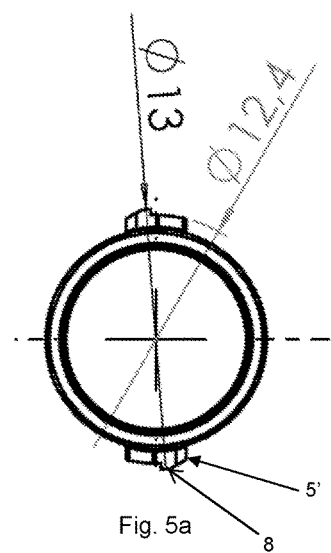
FIGS. 5a-b are schematic illustrations of the cross section of the two ends of the specimen in FIG. 3.
Figure 5B:
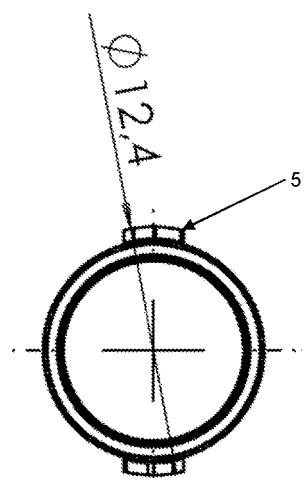
Figure 6:
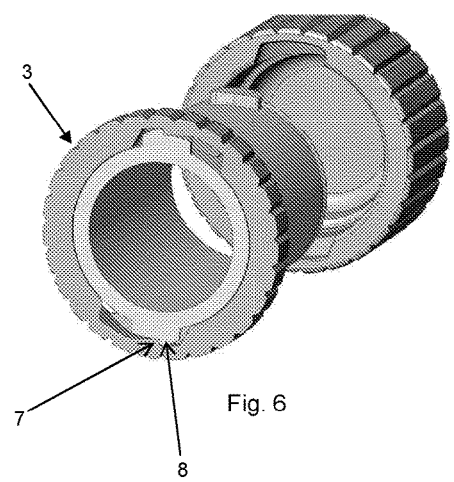
FIG. 6 is a cut-through perspective illustration of the specimen in FIG. 3 with engaging closure caps.

Further, said container 2 is provided with parts 5, 5' of a fastening mechanism, in the illustrated embodiment in FIGS. 1-7 the parts 5, 5' are the male parts of bayonet mounts. The configuration of the parts 5, 5' of the fastening mechanism provided on the storage container 2 varies along the length of the container 2. This is seen by the different configurations of the pins 5, 5'. FIG. 3 shows the specimen 9 isolated from the container 2. One end of the specimen 9 is provided with pin 5 and the opposite end is provided with pin 5'. Pin 5' is provided with a protrusion 8 whereas the surface of pin 5 is substantially flat. This is better illustrated in FIG. 4 which corresponds to FIG. 3 with close-ups of the pins 5, 5' and in FIG. 5 showing end views of the specimen 9 where the difference in cross-section of the pins 5, 5' can be seen. Even though the pins 5, 5' are different they match the same female part of a bayonet mount. The female part is provided in closure caps 3 and can be seen in FIGS. 3, 4 and 6. The closure caps 3 are adapted to engage with the open end of the container 2 and with broken off specimens from the container 2, e.g. the specimen 9 illustrated in FIGS. 3 and 4 by means of the bayonet mount. The female part of the bayonet mount in the closure cap 3 comprises a groove 6 adapted to both pins 5, 5'. A closure cap 3 is mounted by fitting the pins into the groove 6 and subsequently rotating the closure cap 3 and the specimen 9 (or container 2) in relation to each other. The pins 5, 5' then follow inside the groove 6 to engage the specimen 9 and cap 3 in a closed configuration. However, in this closed configuration the protrusion 8 on the pin 5' engages with the protrusion 7 in the groove 6 and provides a locking effect of the cap. The locked configuration with the two engaged protrusions 7, 8 aligned against each other is illustrated in FIG. 6. A closure cap 3 mounted on the opposite end of the specimen 9 with the pin 5 (without protrusion) also provides a closed and tight configuration between the cap 3 and specimen 9. However, with the substantially plane surface of the pin 5 there is no locking effect and the cap 3 can be detached. Thus, if a specimen 9 is provided with closure caps 3 at both ends and one cap is detached by holding the other cap, the cap which is mounted on the end of the specimen 9 with the pin 5 is sure to open because the other cap is locked. When a specimen is closed by two caps it may be difficult to distinguish the different fastenings mechanism. However, by somehow indicating this difference on the surface of the specimen 9 (e.g. by means of an arrow or a simple marking) a user accessing a sample inside the specimen is sure to be able to keep the specimen in the correct vertical orientation and concurrently open the correct cap.

FIG. 2 shows top-view and side view schematic illustrations of the breakable multi-specimen storage vessel of FIG. 1 with a closure cap 3 mounted on the open end 24. The interchanging pins 5, 5' are illustrated along the length of the container and it can also be seen that two pins 5, 5' are located opposite each other across a breakpoint 4 and pins are provided for every 180 degrees round the perimeter of the container 2. Thus, four pins (two of type 5 and two of type 5') are provided adjacent to each breakpoint 4.

Figure 4:
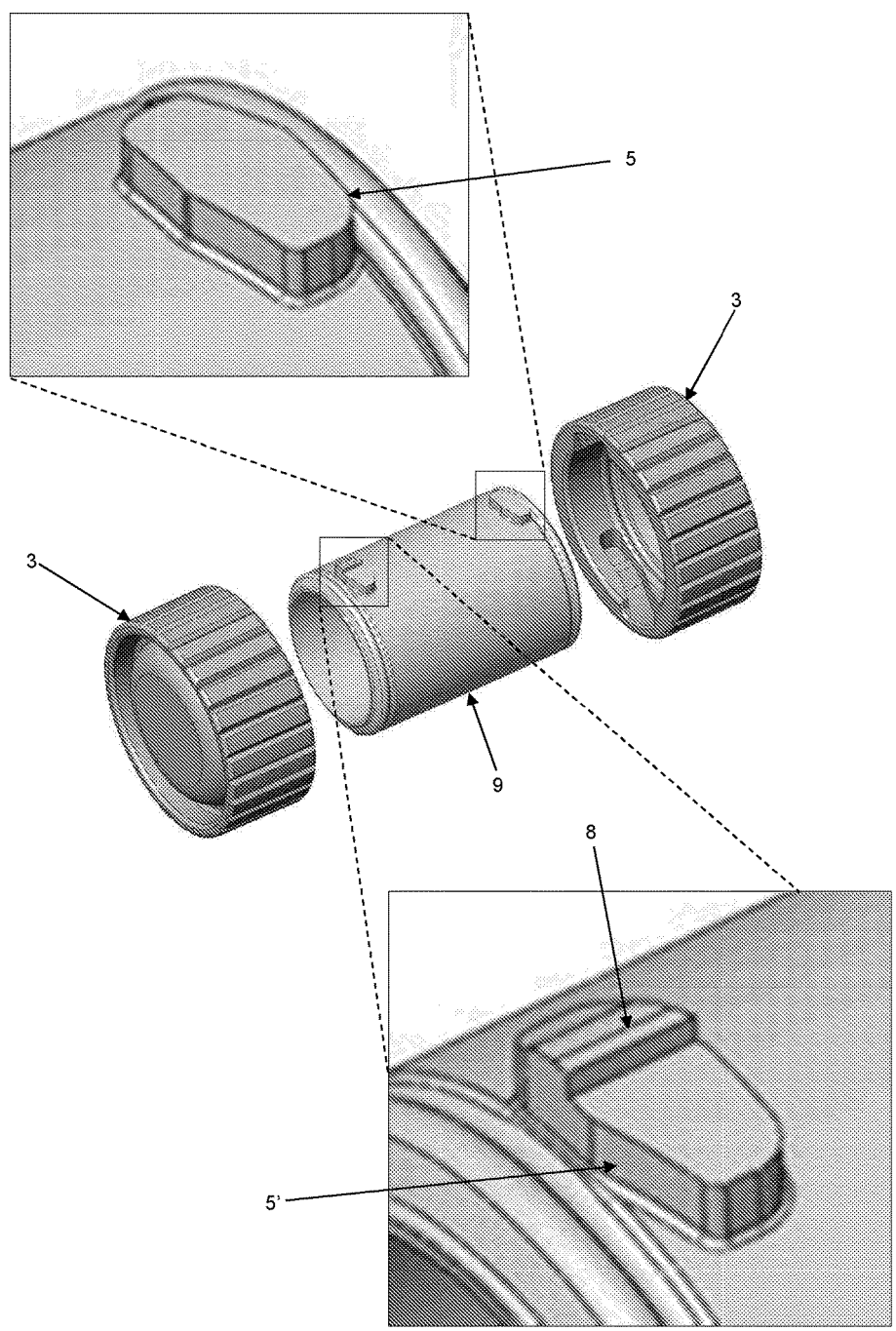
FIG. 4 is the illustration from FIG. 3 with close-ups of the fastening mechanism.

As seen from FIGS. 3, 4 and 6 the cap 3 may be provided with indentations on the outer surface to provide a better grip when mounting and detaching the cap.

FIG. 5 provides a side view of a specimen 9 where the pins are provided opposite each other across the diameter of the specimen 9, i.e. separated by 180 degrees around the circumference of the specimen. The pins 5' in FIG. 5a are provided with a protrusion 8 whereas the pins in FIG. 5b are provided with a protrusion. The values on FIGS. 5a and 5b are the diameter in mm of the specimen measured from the outer surface of the pins, i.e. the diameter from the surface of one pin 5 to the opposite pin is 12.4 mm whereas the diameter from the top of the protrusion 8 to the opposite protrusion is 13.0 mm. Thus, the maximal height of the protrusion 8 is 0.3 mm in this case. The inner and outer diameter of the storage container and (thereby a specimen) is 9 mm and 11 mm, respectively, in this example and the height of a pin 5, 5' is thus 0.7 mm. The corresponding cap 3 has an outer diameter of 14.8 mm and a height of 6.4 mm.

Figure 7B:
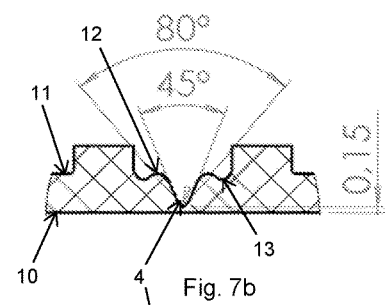
FIGS. 7a-b are detailed schematic illustrations of a break point of one embodiment of the storage vessel according to the invention.
Figure 7A:
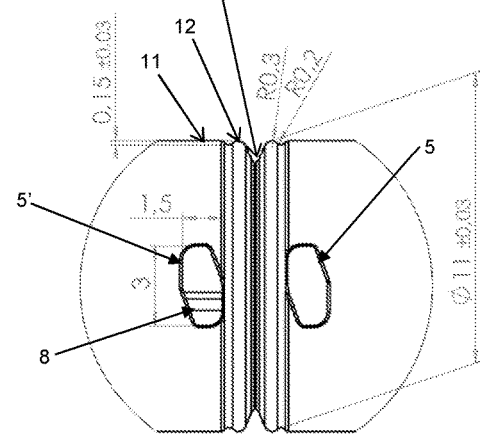

FIG. 7 provides a close-up view of a break-point 4. FIG. 7a is section of the storage container across a break point 4. Pins 5, 5' are visible and they are located adjacent the break point 4, however separated from the actual break portion area. One of the pins 5' comprises a protrusion 8. FIG. 7b is a close-up cross section of the storage container wall across a break point 4. The inner wall/surface 10 of the storage container 2 (or specimen 9) is seen to be smooth across the break point 4. Thus, the break point is constituted by varying the diameter of the outer wall/surface 12 of the container. In this case the thickness of the container wall is 1 mm. At the break point the thickness of the container is 0.15 mm, i.e. at the break point 4 the thickness of the wall is 15% of the container wall. This suffers to provide sufficient strength and stability to the storage container, however at the same time easing the breakage of the container into specimens along the break points 4.

As seen from FIG. 7b the contour of the outer surface of the container across the break point 4 resembles a "double dip" with a small "valley" 13 followed by a top 12 before the large "valley" 4 constituting the break point 4. The top 12 and valley 13 are not necessary to provide the break point, however the top 12 and the valley 13 may help to ensure a tight seal of the specimen when a cap 3 is attached, because the top 12 constitutes a circular lip 12 that can fit into a corresponding circular groove provided inside the cap 3 (this groove is not shown). The lip-groove interlocking mechanism may thereby constitute a snap fastener that provides a liquid and air tight seal between the cap 3 and the specimen 9. In this snap type connection the male part is provided on the specimen whereas the female part is provided integral with the cap. The force necessary to "snap" the male and female part together comes from the rotational movement when mounting the cap 3. When rotating the cap 3 the pins 5, 5' are steered inside the bayonet groove 6 which results in a force that contracts the cap 3 and the specimen 9. This force draws the lip 12 into the corresponding groove and provides the snap fastening and tight seal. A better seal may be provided if a part of the snap type connection is provided in a softer material, providing substantially the same effect as a soft (rubber) gasket or packing (like an o-ring) sealing a closure mechanism. If one part is softer the two part of the snap type connection will better conform to each other possibly resulting in a more tight seal. The soft part may preferentially be provided in the female part of the snap connection, i.e. within the cap 3.

The distances between specimens may be selected appropriately during production relative to the intended use, specimen volume, and user needs. They may be of equal length ranging from between 1 to 100%, preferably from between 10 to 50%, more preferably from 33 to 40% of the entire length of the container 2. The length of a specimen may in many uses correspond to 0.1-0.5 ml volume of sample within the container, depending of course on container diameter at hand, which in principle may be any diameter at hand, but in practice, in particular when applied to cryo tubes, often ranging from 1 mm to 50 mm in diameter. Any number of break portions needed for any type of application is conceivable. Non-equally distanced break portions as shown in FIG. 1 are also conceivable, e.g. for special applications using increasing or decreasing amounts of volume for each test-sample.

The bottom 22 of the container 2 gently curves inwards to form a rounded bottom such as semicircular, convex, cone shaped or pyramidal, in order to provide space e.g. for housing a needle end. The container bottom wall in the container bottom 22 is extending beyond the outer surface of the bottom 22 in order to provide stability, if placed on a plane surface and the bottom 22 extending downwards.

In an alternative embodiment the storage container may be provided with both ends open. Preferably a closure caps are then provided at each end thereof in order to provide a secure fit thereto, reduce spillage, and provide stability standing on one end.

The storage vessel may be broken into two or more specimens during use. The container 2 is designed so that a radially directed gentle manual or machine operated force will break the container 2 along one of the break portions 4. Further, the container 2 is designed such that when the container 2 is divided in a manner that leaves both the lower part and the upper part with a new open end, see FIG. 3, two caps 3 can be attached to these open ends of the container 2.

In FIG. 3 is shown a specimen 9 from the storage vessel of FIG. 1. A biological sample is not known within the storage vessel 1 and specimen 9. However, it may advantageously be used for storing a fluid biological collective sample (not shown) filling out substantially the entire inside volume of the container 2. Further, the vessel comprising the collective sample may preferably be frozen, e.g. for cryogenic use, in order to provide a clean break surface when a specimen is broken off. When broken in a frozen condition, each broken off part will ideally contain frozen specimens, where the exposed surface thereof lies in a substantially flat planar perpendicular relationship to the outer wall surface of the container 2.

The depth of a recess of a break portion 4 is preferably selected relative to the hardness of the material of the container 2 in such a way that both safe storage and handling, and an easy break operation is achieved. The depth of a recess may range between from 5 to 95%, preferably from 50 to 95%, more preferably from 75% to 95% of the total wall thickness of the tubular container 2, depending on container material selected. A remaining wall thickness of 5 to 25% is sufficient for maintaining container stability and securing handling. The shape of the recesses may be v-shape, u-shape, ]-shape or any other appropriate shape, and/or may differ or be of uniform shape along the container 2.

An outer surface of at least part of said container 2 or specimen 9 may further include information such as markings identifying at least the specimen 9 taken, and/or identifying which vessel said specimen has been taken from, e.g. a three to five digit (number, letter, symbol) code or codes in sequence extending peripherally and/or longitudinally along the longitudinal side thereof or the like. When being delivered in a collection of 100 to 1000 pieces of such storage vessels, the sequence of digits is preferably selected in such batch as not to result in any duplicate digit combination thereon. Thus, the risk of mix-up between specimens broken off and the remainder of the vessel before labelling thereof has been performed may be reduced, as it could happen in the case of dropping or misplacing one or more of said specimens.

Further, at least part of an outer container 2 surface and/or outer cap 3 surface may be provided with volume indication markings of the volume within, in sequence or using simple perimeter line markings, as is known to the skilled person. They may correspond to relatively small volumes, such as 0.1 ml each or larger volumes, such as from 0.1 ml up to 1 dl, depending on length and diameter of the container being used.

Further, the vessel may be provided with further info, such as trademarks, producer name, and the like. The markings may include a planar longitudinally extending section for providing an adhesive ID label or barcode e.g. for individual specimen identification, date and/or user initials. The different types of markings may for example comprise written information, a number, barcode, and/or sign indication sequence, or any combination thereof, also stating production info, producer ID, and may be provided by labelling, moulding, etching, cutting or milling.

Further, the cap form, i.e. diameter and design of sides fits snugly with the wall of the container in such a way that an easy fastening on of the cap is provided, and such that a secure tightening is allowed, for a secure fit of the cap to the container. One or more of the caps 3 may preferably be supplied together with one or more of said containers 2 to constitute a storage vessel according to the invention.

The storage vessel, e.g. the tubular container 2 and one or more caps 3, should all be made of materials which can withstand deep freezing temperatures and which have got reduced resistance against radial breakage at least deep frozen. In general, a chemical resistant material is preferred, where some preferred materials include plastic materials such as polypropylene (PP), polyethylene (PEHD), polystyrene, or polycarbonate, but some glass materials resistive to temperature variances may also come into use. The caps and/or the container may further comprise rubber or plastic gaskets suitable for sealing during cryogenic temperatures.

The material used for the tubular container 2 may preferably chosen as to be easily mouldable and/or workable for providing break portions, such as cuts and/or threads therein, which are both durable during storage and handling, and easily breakable during dividing. The material may then preferably be chosen as polypropylene, because this material has increased brittleness during freezing temperatures.

Further, in order to provide excellent security against spillages, the cap 3, at least in room temperatures, may be of a more or less resilient and/or more or less hard material than the container 2, or vice versa. The material of the cap 3 may be softer than the material of the container 2 at room temperature and/or during breakage temperature, such as cryogenic temperatures, i.e. around −70° C., or even higher temperatures, e.g. around 0° C., or higher yet. Further, the material of the cap 3 may be harder than the material of the container 2 at room temperature and/or during freezing temperature. That is to say that the hardness of the material of the cap 3 and/or container 2 may be chosen as to ease the application and detachment of the cap 3 from the container 2, while at the same time provide a secure fit therebetween.

In order to increase readability of the volume or ID markings upon the container 2, the cap 3 or caps may be provided in a transparent material.

The container may be produced by moulding, e.g. blow or injection moulding or the like, as is known to the skilled person, and different elements of the container, such as the threads, the markings, the recesses and/or the side extensions my be provided at the same time or machined after moulding. If more than one material is needed, e.g. two materials of different hardness, multi component injection moulding is a good choice.

The break portions 4 of the container 2 may be specifically indicated, e.g. using peripheral colour line markings, metal or magnetic band marking, e.g. for use in further processing, or the like, for a further visual indication of the position of the break portion. A storage vessel according to the invention is designed to be broken off into specimens using a manual break operation, but may also broken using a break tool, in which case, the risk of breakage in a wrong position or damage to the container is decreased. Examples of such possible break tools will be described below are described in WO 2009/086829 by the same inventors.

During use, the cap 3 is applied, for example during a frozen state by mounting the cap 3. Then the cap 3 and container 2 is held by the user in each hand and broken into two parts by using the necessary break force. Other alternatives are conceivable, for example a break tool is held fixed against a surface, such as a table or a wall, and the user breaks the specimen off using manually applied force, or the breaking off is performed automatically or manually using a force providing means, such as a motor operated winch, pawl or pin (not shown).

The invention claimed is:

1. A breakable multi-specimen storage vessel comprising:
   a container comprising a lower end and an upper end, at least one end having an open end, the length of said container being continuously formed and provided with break portions at predetermined positions alongside thereof where said container is adapted to be broken into a plurality of specimens, each specimen having a first end provided with at least a part of a first fastening mechanism and a second end provided with at least a part of a second fastening mechanism, wherein the configuration of the first fastening mechanism is different from the configuration of the second fastening mechanism; and
   a closure adapted to close the container and/or one or more of said specimens;
   wherein the part of the first fastening mechanism provided on the first end of a specimen and the part of the second fastening mechanism provided on the second end of a specimen are adapted to fasten to the same closure.

2. The storage vessel according to claim 1, wherein the container has a circular or elliptical cross section.

3. The storage vessel according to claim 1, wherein the first or the second fastening mechanism is a locking mechanism.

4. The storage vessel according to claim 1, wherein the tension of the first fastening mechanism is different from the tension of the second fastening mechanism.

5. The storage vessel according to claim 1, wherein the tension necessary to release the first fastening mechanism is different from the tension necessary to release the second fastening mechanism such that one of the fastening mechanisms requires less tension or force to reopen than the opposite end.

6. The storage vessel according to claim 1, wherein the closure and/or the ends of a breakpoint are further provided with a seal adapted to seal the connection between the closure and the container and/or one or more of said specimens.

7. The storage vessel according to claim 6, wherein said seal is at least a part of a snap type connection, said snap type connection preferably comprising a "plug" (male part) fitting into a "socket" (female part).

8. The storage vessel according to claim 7, wherein each end of a specimen comprises or constitutes a male part of said snap connection and where the corresponding female part of said snap connection is provided integral with the closure.

9. The storage vessel according to claim 6, wherein said seal comprises a material that is softer than a material of a remainder of the closure.

10. The storage vessel according to claim 6, wherein said seal is at least partly provided in a material that is softer than a material of a remainder of the closure.

11. The storage vessel according to claim 7, wherein the female part of the snap type connection is at least provided in a material that is softer than a material of a remainder of the closure.

12. The storage vessel according to claim 1, wherein the part of the first and/or second fastening mechanism provided on the ends of a specimen is provided on an outer surface of said specimen.

13. The storage vessel according to claim 1, wherein the first and/or the second fastening mechanism is a bayonet mount.

14. The storage vessel according to claim 1, wherein the part of the first and second fastening mechanism provided on the first and second end of each specimen, respectively, is the male side of a bayonet mount.

15. The storage vessel according to claim 14, wherein at least one pin of the bayonet mount is provided with a first protrusion.

16. The storage vessel according to claim 15, wherein the closure comprises the female side of the corresponding bayonet mount, said female part comprising a groove adapted to match the corresponding male side and a second protrusion in said groove adapted to engage with said first protrusion in the male part.

17. The storage vessel according to claim 1, wherein the closure is one or more caps adapted to engage with the container and/or one or more of said specimens.

18. The storage vessel according to claim 17, wherein at least one of said caps is a snap cap.

19. The storage vessel according to claim 17, wherein at least one of said caps is provided with an internal curving bottom.

20. The storage vessel according to claim 17, wherein a material of the cap is softer than a material of the container or a material of the cap is harder than a material of the container.

21. The storage vessel according to claim 1, wherein said break portions are provided as one or more ring-shaped external recesses extending around a perimeter of said container.

22. The storage vessel according to claim 1, wherein the container is adapted to be broken into to a plurality of specimens upon application of a radially directed force.

23. The storage vessel according to claim 21, wherein the depth of said one or more ring-shaped external recesses is from 50% to 95%, or from 70% to 95%, or from 80% to 90% of the total wall thickness of said container.

24. The storage vessel according to claim 1, wherein an internal surface of said container is smooth.

25. The storage vessel according to claim 1, wherein a material of the container and/or the cap is a plastic material or a glass material.

26. The storage vessel according to claim 1, further comprising identification marks for indicating the different fastening mechanisms.

27. The storage vessel according to claim 1, further comprising identification marks on each specimen for indicating the different fastening mechanisms.

28. The storage vessel according to claim 1, wherein said storage vessel is a cryogenic storage vessel.

29. The storage vessel according to claim 3, wherein upon closing of the container, the end having the locking mechanism cannot be reopened.

30. The storage vessel according to claim 5, wherein one of the fastening mechanisms requires less tension or force to reopen than the fastening mechanism of the opposite end.

31. A method for closing and safely reopening a container, the method comprising the steps of:
providing a container including at least two open ends, wherein a first end is provided with at least a part of a first fastening mechanism and a second end is provided with at least a part of a second fastening mechanism, and wherein the configuration of the first fastening mechanism is adapted to be different from the configuration of the second fastening mechanism, the length of the container being continuously formed and provided with break portions at predetermined positions alongside thereof where the container is adapted to be broken into a plurality of specimens;
providing a closure adapted to close the container and/or one or more of said specimens;
wherein the part of the first fastening mechanism provided on the first end of a specimen and the part of the second fastening mechanism provided on the second end of a specimen are adapted to fasten to the same closure.

32. The method for closing and safely reopening a container according to claim 31, wherein the first or the second fastening mechanism has a locking mechanism such that upon closing of the container, the end having the locking mechanism cannot be reopened.

33. The method for closing and safely reopening a container according to claim 31, wherein the tension necessary to release the first fastening mechanism is different from the tension necessary to release the second fastening mechanism such that one of the fastening mechanisms requires less tension or force to reopen than the fastening mechanism of the opposite end.

* * * * *